(12) United States Patent
Leibovici et al.

(10) Patent No.: US 6,482,417 B2
(45) Date of Patent: Nov. 19, 2002

(54) STABLE PHARMACEUTICAL FORMULATION COMPRISING TORSEMIDE MODIFICATION II

(75) Inventors: Minutza Leibovici, Netanya (IL); Ruth Tenengauzer, Hod HaSharon (IL); Mira Kopel, Pardess Hanna (IL); Judith Aronhime, Rechovot (IL); Marco Kordova, Kfar Saba (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

(21) Appl. No.: 09/789,424

(22) Filed: Feb. 21, 2001

(65) Prior Publication Data

US 2002/0035135 A1 Mar. 21, 2002

Related U.S. Application Data

(60) Provisional application No. 60/183,288, filed on Feb. 17, 2000.

(51) Int. Cl.[7] .................................................. A61K 9/00
(52) U.S. Cl. ........................................ 424/400; 424/464
(58) Field of Search ................................. 424/464, 465, 424/400; 514/347

(56) References Cited

U.S. PATENT DOCUMENTS

| | | | |
|---|---|---|---|
| RE30,633 E | | 6/1981 | Delarge et al. |
| 4,822,807 A | | 4/1989 | Topfmeier et al. |
| RE34,672 E | | 7/1994 | Topfmeier et al. |
| 5,738,872 A | * | 4/1998 | Ortyl et al. .................. 424/452 |
| 5,914,336 A | * | 6/1999 | Dreckmann-Behrendt .. 514/347 |

OTHER PUBLICATIONS

Acta Crystallographica, vol. B34 Part 4, Apr. 15, 1978 (pp. 1051–1400).
Acta Crystallographica, vol. B34 Part 8, Aug. 15, 1978 (pp. 2387–2672).

* cited by examiner

Primary Examiner—Jose' G. Dees
Assistant Examiner—Sharmila S. Gollamudi
(74) Attorney, Agent, or Firm—Kenyon & Kenyon (57) ABSTRACT

Novel, stable pharmaceutical formulations for the oral administration of high purity torsemide modification II are disclosed. These formulations release high purity torsemide modification II in water at a constant and high purity rate, and the high purity torsemide modification II therein does not rearrange to torsemide modification I over time. Methods for their manufacture are also disclosed.

19 Claims, 3 Drawing Sheets

STABLE PHARMACEUTICAL FORMULATION COMPRISING TORSEMIDE MODIFICATION II

CROSS-REFERENCE TO RELATED APPLICATION

This application claims the benefit of provisional application Ser. No. 60/183,288, filed Feb. 17, 2000, the contents of which are incorporated herein by reference.

FIELD OF THE INVENTION

The present invention relates to the formulation of pharmaceutical compositions, and more particularly to novel pharmaceutical formulations for the oral administration of torsemide.

BACKGROUND OF THE INVENTION

1-Isopropyl-3-[(4-m-toluidino-3-pyridyl)-sulfonyl]urea, which is represented by the structural formula $C_{16}H_{20}N_4O_3S$ is approved, under the trademark DEMADEX®, by the U.S. Food and Drug Administration, for the treatment of hypertension and edema associated with congestive heart failure, renal disease, or hepatic disease. The USAN approved generic name for this compound is torsemide, although this compound is also referred to as "torasemide" in the art. Torsemide is a loop diuretic that has been found to be particularly effective for the treatment of edema associated with chronic renal failure.

U.S. Pat. No. Re. 30,633 describes a synthesis of torsemide. It is known that torsemide can occur in at least two different crystalline forms, Acta Cryst. 1978, pp. 2659–2662 and Acta Cryst., 1978, pp. 1304–1310, in which the crystal identified by space group $P2_1/c$ is designated Dupont Form 1 herein and the crystal identified by space group P2/n is designated Dupont Form 2 herein. U.S. Pat. No. 4,822,807, which reissued as U.S. Pat. No. Re. 34,672, describes two crystalline forms of torsemide, designated modification I and modification II. Torsemide modification I is defined herein as the torsemide characterized by the x-ray powder diffraction pattern of FIG. 1, in the 37 C.F.R. § 1.132 declaration by Dr. Fritz Topfmeier filed on Dec. 30, 1987, which is located in the file wrapper of U.S. Pat. No. 4,822,807 (the "Topfmeier Declaration"). Torsemide modification II is defined herein as the torsemide characterized by the x-ray powder diffraction pattern of FIG. 2, in the Topfmeier Declaration.

Topfmeier and Lettenbauer have described in U.S. Pat. No. 4,822,807 that when torsemide of modification II is present in very finely divided form in pharmaceutical tablets, it rearranges into torsemide modification I, with the result that the rate of dissolution of the active material upon introducing the tablets into water can be significantly changed. The dissolution rate is an important characteristic of a pharmaceutical dosage form and, in order to dose reproducibly, must not differ from one tablet to the next.

Thus, there remains a need in the art for pharmaceutical formulations containing torsemide modification II, wherein the torsemide does not rearrange into torsemide modification I and that are stable with regard to dissolution rate.

SUMMARY OF THE INVENTION

Stable pharmaceutical formulations containing torsemide modification II, wherein, upon storage under stress conditions, the torsemide modification II does not rearrange into torsemide modification I and wherein the stable pharmaceutical formulations are also stable with regard to dissolution rate in solution, have been discovered.

Additionally, a high purity torsemide modification II which is substantially free of other forms of torsemide and processes for making the high purity torsemide modification II have also been discovered.

The present invention relates to high purity torsemide modification II that does not substantially rearrange into a different form of torsemide over time upon storage in bulk under stress conditions, e.g., 40° C., 75% relative humidity. Preferably, the high purity torsemide modification II does not substantially rearrange into torsemide modification I over time upon storage in bulk under stress conditions, e.g., 40° C., 75% relative humidity.

The present invention also relates to a stable pharmaceutical formulation comprising an effective amount of torsemide modification II and a pharmaceutically acceptable excipients wherein the excipients have a low moisture content. Preferably, the stable pharmaceutical formulation further comprises the excipients lactose anhydrous, crospovidone, povidone, microcrystalline cellulose, and magnesium stearate all of which having a low moisture content. Preferably, the stable pharmaceutical formulation comprises torsemide modification II in an amount of about 2.5 mg to about 200 mg per tablet. More preferably, the stable pharmaceutical formulation comprises torsemide modification II in an amount of 2.5 mg, 5 mg, 10 mg, 20 mg or 100 mg.

The present invention also relates to stable pharmaceutical formulations comprising an effective amount of torsemide modification II wherein the torsemide modification II does not substantially rearrange into another form of torsemide over time upon storage under stress conditions, e.g., 40° C., 75% relative humidity. Preferably, the torsemide modification II of the stable pharmaceutical formulations does not substantially rearrange into torsemide modification I over time upon storage under stress conditions. Torsemide modification II suitable for use in the present stable pharmaceutical formulations includes high purity torsemide modification II and torsemide modification II containing trace amounts of torsemide modification I. Trace amounts, as defined herein, are amounts of torsemide modification I that are about 0.5–2% by weight of the torsemide modification II (w/w % of torsemide modification I/torsemide modification II).

The present invention relates to stable pharmaceutical formulations comprising an effective amount of torsemide modification II wherein the torsemide modification II has a particle size distribution such that 100% is below 200 μ. Preferably, the particle size distribution is such that 100% is below 100 μ. More preferably, the particle size distribution is such that 100% is below 50 μ.

The present invention also relates to stable pharmaceutical formulations comprising an effective amount of torsemide modification II wherein the dissolution rate in vitro of the stable pharmaceutical formulation, when measured by the U.S.P. Paddle Method at 50–90 RPM in 900 mL water, is not less than 80% (by weight) of the torsemide modification II released after 30 minutes. Preferably, the dissolution rate in vitro does not substantially change over time upon storage in bulk under stress conditions, e.g., 40° C., 75% relative humidity. More preferably, the dissolution rate in vitro does not substantially change during storage under stress conditions for at least 3 months.

The present invention also relates to a process for making high purity torsemide modification II wherein the high purity torsemide modification II is purified from crude modification II by the novel combination of two purification steps known in the art wherein the novel process comprises the steps of (1) reslurrying crude torsemide modification II followed by (2) crystallization to yield high purity torsemide modification II by the methods of U.S. Ser. No. 09/638,106; filed Aug. 11, 2000, the contents of which are incorporated herein by reference

DETAILED DESCRIPTION OF THE INVENTION

The present invention relates to high purity torsemide modification II wherein the high purity torsemide modification II has the surprising and useful advantage of being a stable polymorphic form of torsemide, that is, it does not substantially rearrange over time, thereby making high purity torsemide modification II of the present invention useful for the manufacture of stable pharmaceutical tablets of torsemide modification II. Preferably, the high purity torsemide modification II is in the form of fine crystal. Preferably, the high purity torsemide modification II does substantially rearrange over time into torsemide modification I (such as not more than 10% of torsemide modification II rearranges to torsemide modification I).

The high purity torsemide modification II of the present invention may be in the form of fine crystals. The high purity torsemide modification II may be further characterized by having a particle size distribution such that 100% is below 200 $\mu$. Preferably, the particle size distribution is such that 100% is below 100 $\mu$. More preferably, the particle size distribution is such that 100% is below 50 $\mu$.

It was surprisingly found that when torsemide modification II is crystallized as high purity torsemide modification II, with no trace amounts of torsemide modification I, the high purity torsemide modification II is stable during storage under stress conditions for at least 3 months. In contrast, torsemide modification II that contains trace amounts of torsemide modification I is not stable during storage under stress condition for at least 3 months. The torsemide modification II containing trace amounts of torsemide modification I rearranges into torsemide modification I over time during storage under stress conditions.

Significantly, it has been found that upon storage at 40° C., 75% relative humidity, for 3 months, the polymorphic content of high purity torsemide modification II of the tablet formulations, or the bulk active ingredient, does not undergo any significant rearrangement into different polymorphic forms of torsemide. Preferably, not more than 10% of the high purity torsemide modification II rearranges into different polymorphic forms of torsemide following storage of the tablets or bulk active ingredient. More preferably, not more than 5% of the high purity torsemide modification II rearranges into different polymorphic forms. Even more preferably, not more than 2% of the high purity torsemide modification II rearranges into different polymorphic forms and most preferably, the high purity torsemide modification II is substantially pure polymorph torsemide modification II following storage. Specifically, the high purity torsemide modification II of the present invention does not undergo a polymorphic rearrangement into torsemide modification I. The detection of torsemide modification I in bulk high purity torsemide modification II or tablets of high purity torsemide modification II may be accomplished by using x-ray powder diffraction techniques. No substantial polymorphic change of the high purity torsemide modification II of the present pharmaceutical formulations or present bulk active ingredient can be detected by x-ray powder diffraction techniques.

Without being bound by theory, it is believed that the level of purity presently achieved in the high purity torsemide modification II imparts the polymorph with unexpected stability. It is feasible that the unstable torsemide modification II described in the relevant art contains trace amounts of torsemide modification I, the presence of which facilitates the rearrangement of torsemide modification II into torsemide modification I. It has been reported in the art that trace amounts of torsemide modification I facilitates the conversation of torsemide modification II into torsemide modification I when in an aqueous suspension.

The present invention also relates to a novel and stable pharmaceutical formulation containing fine crystals of torsemide modification II wherein the present stable pharmaceutical formulations have the surprising and useful advantage that the active material, torsemide modification II, does not substantially rearrange into torsemide modification I (such as not more than 5% of torsemide modification II rearranges to torsemide modification I), thereby making the stable pharmaceutical formulations of the present invention useful for the administration of torsemide modification II. The pharmaceutical formulations of the present invention are solid dosage forms for the oral administration of torsemide that are presented as a tablet.

Surprisingly, it was also found that the pharmaceutical formulation containing use of Excipient with a low water content stablizes modification II.

The present invention also provides methods for making stable pharmaceutical formulations torsemide modification II which are tablets. High purity torsemide modification II tablets are prepared by mixing the active ingredient, torsemide modification II, with a combination of excipients including, lactose anhydrous NF, crospovidone NF, povidone USP (PVP K-30), and microcrystalline cellulose NF (Avicel PH 112). Alcohol 95% USP is added to the powder mixture of torsemide modification II and excipients. The mixture is then dried until only trace amounts of fluid remain in the granulate as residual moisture. Preferably, the mixture is dried to 0.5–1.5% moisture content. The granulate is then sieved, and magnesium stearate is added to the milled granulate. The final blend of torsemide modification II, excipients and magnesium stearate is compressed into tablets on a rotary tableting machine. Table 1 shows suitable ranges of active ingredients and excipients (weight %) and the preferred amounts for the present pharmaceutical formulations.

While not being bound by theory, it is believed that the observed unexpected stability of torsemide modification II (which is not high purity torsemide modification II) in the present pharmaceutical formulation is achieved by the present novel formulation which serves to inhibit the rearrangement of torsemide modification II into torsemide modification I.

TABLE 1

| Material | Range of % composition (w/w) | Preferred % composition | Function |
| --- | --- | --- | --- |
| High purity Torsemide modification II | 2.5–25% | 5% | active ingredient |
| Lactose Anhydrous NF | 25.5–65% | 45.5% | filler |
| Crospovidone NF | 10–15% | 12.0% | disintegrant |
| Povidone USP (PVP K-30) | 1–3% | 1.5% | binder |
| Microcrystalline Cellulose NF (Avicel PH 112) | 25–45% | 35.0% | filler and disintegrant |
| Alcohol 95% USP* | — | — | Granulation processing solvent |
| Magnesium Stearate NF | 0.5–2.5% | 1.0% | lubricant |

*Granulation processing solvent only (dried to achieve moisture content of 0.5–1.5%).

Significantly, it has also been found that the pharmaceutical formulations of the present invention containing fine crystals of high purity torsemide modification II have a dissolution rate in water and in potassium phosphate buffer that does not substantially change over time. It has been found that the tablet formulations of the present invention, during storage at 40° C., 75% relative humidity, for 6 weeks, do not undergo any substantial change in the dissolution rate. The dissolution rate was determined by the U.S.P. Paddle Method, 37° C., 90 RPM, 0.01M $KH_2PO_4$, pH 4.5; and by the U.S.P. Paddle Method, 37° C., 50 RPM, purified water.

In accordance with the present invention, the pharmaceutical formulations of the present invention are useful for the treatment of hypertension and edema associated with congestive heart failure, renal disease, or hepatic disease. While one of ordinary skill in the art will understand that dosages will vary according to the indication, age of the patient, and other factors, generally the formulations of the present invention will be administered at a daily dosage of the active ingredient between about 2 to about 200 mg per day, and preferably about 5 mg to about 100 mg per day. As torsemide is suitable for once-daily dosing, preferably each unit dosage form will contain between about 5 mg and about 100 mg.

EXAMPLES

The pursuant invention will now be further explained in the following examples. However, the present invention should not be construed as limited thereby.

Determination of Polymorphic Content by X-Ray Powder Diffraction Analysis Bulk High Purity Torsemide Modification II (Bulk Nol 851700100)

| Polymorph Content Storage Conditions | | Length of Storage |
| --- | --- | --- |
| 55° C. | 40° C., 75% RH | t = 0 |
| Polymorphic form detected (I or II) | | |
| II | | 1 week |
| II | II | 2 weeks |
| II | II | 1 month |
| II | II | 2 months |
| II | II | 3 months |
| II | II | 4 months |

Determination of Polymorphic Content by X-Ray Powder Diffraction Analysis Bulk Torsemide Modification II (II) with trace amounts of Modification I (I) (Bulk Nol 851700200)

| Polymorph Content Storage Conditions II >>> I(<0.3%) | | Length of Storage t = 0 |
| --- | --- | --- |
| II >> I (≈0.4%) | | 1 week |
| I + II | II >> I (≈0.5%) | 2 weeks |
| I + II | II >> I (≈1%) | 1 month |
| I + II | II >> I (≈6%) | 2 months |
| I > II | I + II | 3 months |
| I + II | I + II | 4 months |

Example 1

X-Ray Powder Diffraction (XRPD) Method for the Detection and Quantification of Torsemide Modification I in Torsemide Modification II 1. The present procedure is used for the detection and quantitative determination of the presence of torsemide modification I in tablets wherein the active ingredient is high purity torsemide modification II. The present procedure is also used for the detection and quantitative determination of torsemide modification I in bulk high purity torsemide modification II, which is to be used as the active ingredient in tablets. The present method is based on the unique x-ray powder diffraction pattern of torsemide modification I that is characterized by a strong peak at two-theta 5.7±0.20°, the presence of which indicates the presence of torsemide modification I in a sample of high purity torsemide modification II.

2. EQUIPMENT 2.1 Instrument: Philips x-ray powder diffractometer. Goniometer model PW 1050/70, Cu-tube, curved graphite monochromator.

2.2 Sample holder: A standard aluminum sample holder with a rectangular cavity 20*15*0.3 mm inside it.

3. RUN PARAMETERS

Scanning range: $2\theta=4°$ to at least 22°

Step: 0.05°

Step duration: 0.5

4. PROCEDURE FOR SAMPLE PREPARATION 4.1 Gently grind a small amount of sample powder in an agate mortar with the pestle.

4.2 Fill the rectangular cavity on the sample holder with the powder.

Figure 1:
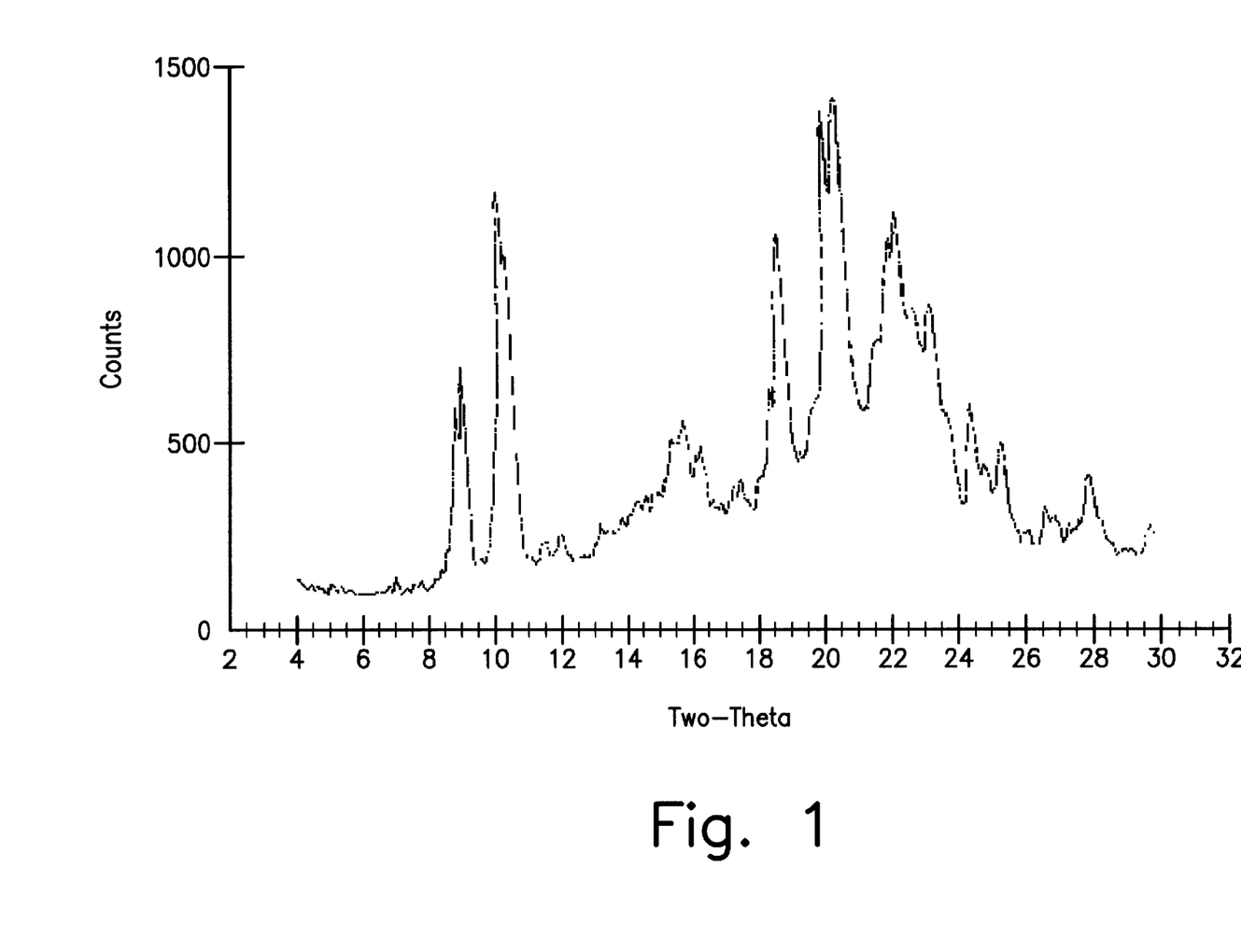
FIG. 1 is an x-ray powder diffraction pattern of a high purity torsemide modification II tablet (Batch No. K-26683).
Figure 2:
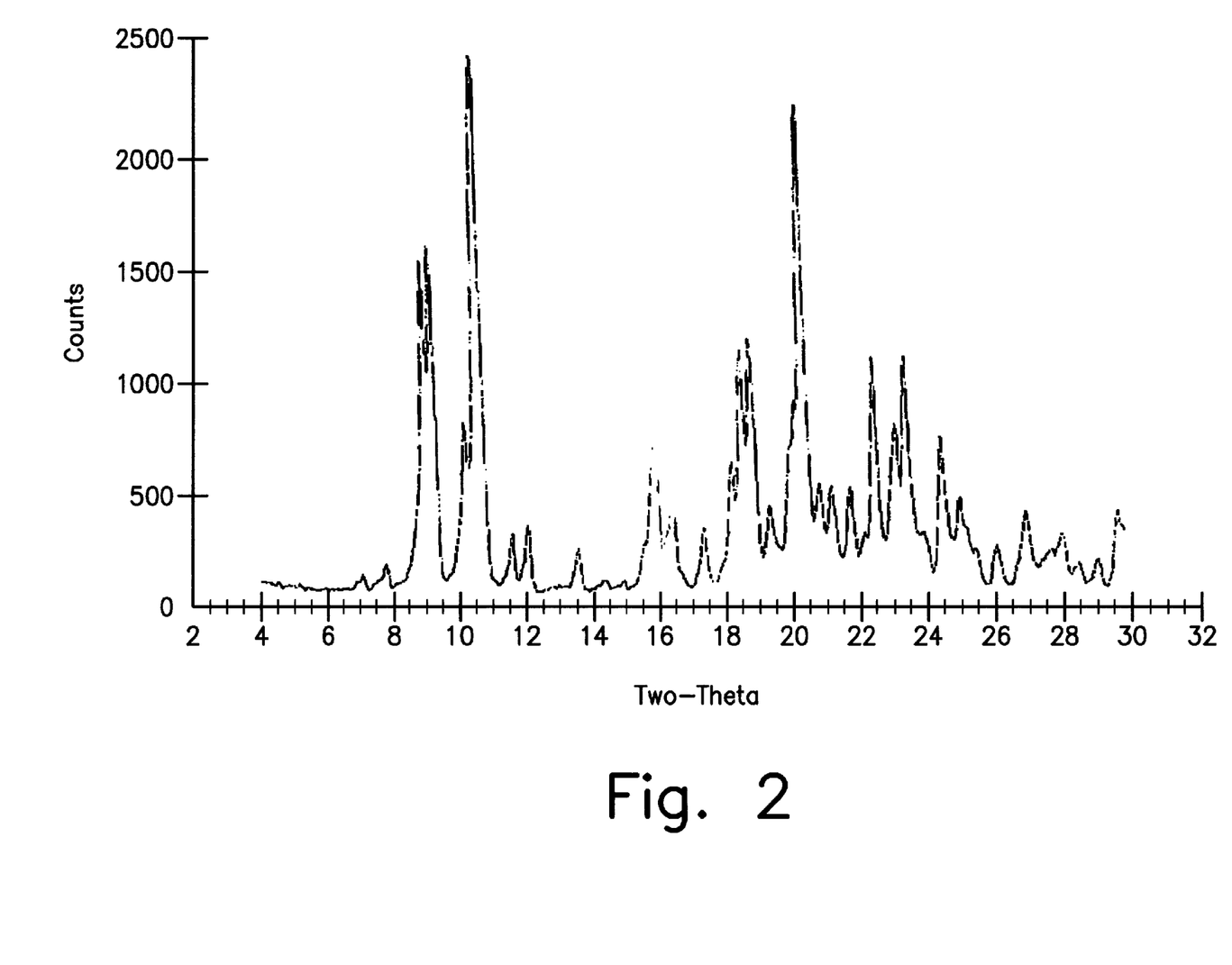
FIG. 2 is an x-ray powder diffraction pattern of bulk high purity torsemide modification II (API 851700100).
Figure 3:
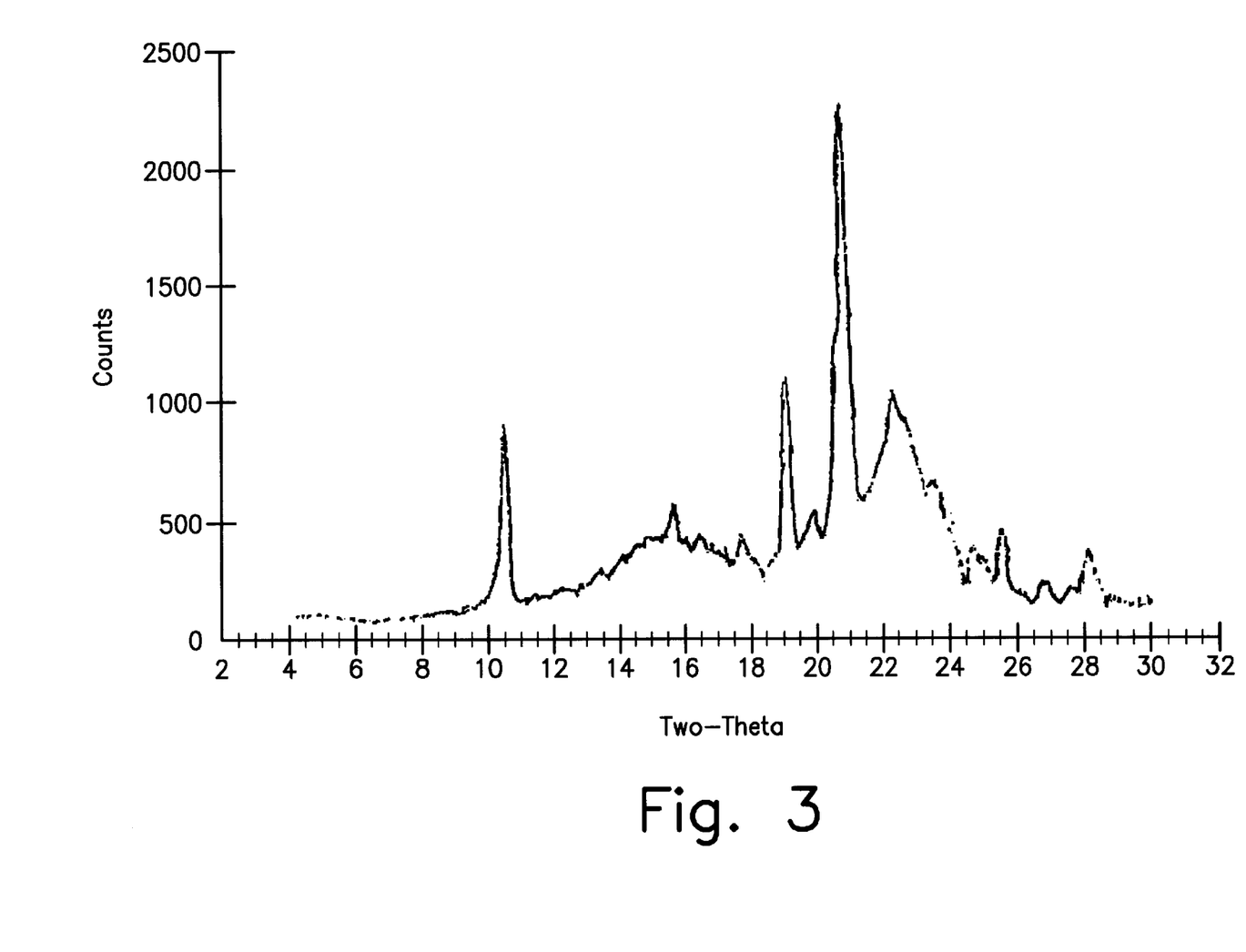
FIG. 3 is an x-ray powder diffraction pattern of a placebo tablet corresponding to a tablet containing 100 mg of high purity torsemide modification II.

Stability Results for Torsemide Tablets K-26058 and K-26683 Containing 100 mg of Active Ingredient Tablets containing 100 mg of high purity torsemide modification II, prepared according to the methods of Example 2, were stored under stressed conditions (40° C., 75% relative humidity). The polymorphic content of torsemide inside the tablet was monitored by x-ray powder diffraction (XRPD) techniques. Representative x-ray powder diffraction patterns are shown in the Figures. FIG. 1 is an x-ray powder diffraction pattern of a high purity torsemide tablet (Batch No. K-26683). FIG. 2 is an x-ray powder diffraction pattern of bulk high purity torsemide modification II (API 851700100). FIG. 3 is an x-ray powder diffraction pattern of a placebo tablet corresponding to a tablet containing 100 mg of high purity torsemide modification II and therefore contains no torsemide. The XRPD of a 100 mg tablet of Batch No. K-26683 directly following production, t=0, showed XRPD peaks typical of high purity torsemide modification II. The XRPD of the K-26683 tablet following three months of storage at 40° C. and 75% relative humidity showed XRPD peaks typical of high purity torsemide modification II and did not show an XRDP peak at 5.7 degrees two-theta, which would indicate the presence of torsemide modification I. Similarly, the XRPD of a 100 mg tablet of Batch No. K-26058 directly following production, t=0, showed XRPD peaks typical of high purity torsemide modification II. The XRPD of the K-26058 tablet following three months of storage at 40° C. and 75% relative humidity showed XRPD peaks typical of torsemide modification II and did not show an XRPD peak at 5.7 degrees two-theta, which would indicate the presence of torsemide modification I. The diffraction peaks at 20.4 and the broad peak at about 22.5 degrees two-theta are characteristic of the filler.

Lower dosage tablets, for example, tablets containing 10 mg of high purity torsemide modification II, were stored for 2 months at 40° C., 75% relative humidity, and were monitored by solid state NMR. The resulting solid state NMR data indicated that the high purity torsemide modification II of the lower dose tablets did not substantially rearrange.

Example 2

Manufacturing procedure

In a high speed mixer, high purity torsemide modification II was mixed with lactose anhydrous NF, crospovidone NF, povidone USP, and microcrystalline cellulose NF. Alcohol 95% USP was added to the powder mixture. The wet granulate mixture was dried in a fluid bed drier at 50° C. to a loss on drying (LOD) of 0.5–2.0%. The resulting dry granulate of high purity torsemide modification II was then sifted through a 0.8 mm sieve and magnesium stearate NF was added to the milled granulate. The final blend of high purity torsemide modification II, excipients and magnesium stearate was compressed into oval shaped tablets on a rotary tableting machine.

| Example 2A. High purity Torsemide Tablets (2.5 mg) | |
|---|---|
| Composition (Batch No. K-26056) | grams per 15,000 tablets |
| High Purity Torsemide Modification II | 37.5 |
| Lactose Anhydrous NF | 697.5 |
| Crospovidone NF | 150.0 |
| Povidone USP (PVP K-30) | 37.5 |
| Microcrystalline Cellulose NF (Avicel PH 112) | 52.5 |
| Alcohol USP | 500.0 |
| Magnesium Stearate NF | 12.8 |

| Example 2B. High purity Torsemide Tablets (5 mg) | |
|---|---|
| Composition (Batch No. K-26057) | grams per 15,000 tablets |
| High Purity Torsemide Modification II | 75 |
| Lactose Anhydrous NF | 697.5 |
| Crospovidone NF | 150.0 |
| Povidone USP (PVP K-30) | 37.5 |
| Microcrystalline Cellulose NF (Avicel PH 112) | 52.5 |
| Alcohol USP | 510.0 |
| Magnesium Stearate NF | 14.6 |

| Example 2C. High purity Torsemide Tablets (100 mg) | |
|---|---|
| Composition (Batch No. K-26058) | grams per 3,750 tablets |
| High Purity Torsemide Modification II | 375.0 |
| Lactose Anhydrous NF | 547.0 |
| Crospovidone NF | 150.0 |
| Povidone USP (PVP K-30) | 37.5 |
| Microcrystalline Cellulose NF (Avicel PH 112) | 375 |
| Alcohol USP | 616.0 |
| Magnesium Stearate NF | 15.0 |

Example 3

Dissolution Results

The dissolution method used was the U.S.P. Paddle Method, at 90 RPM with 0.1M $KH_2PO_4$, pH 4.5 at 37° C. For the dissolution test, 6 tablets were tested in 900 mL of phosphate buffer, pH 4.5, according to the Paddle Method of the U.S.P. Examples 3A, 3B and 3C show the dissolution rates of three tablet lots directly after production and after 6 weeks of storage at 40° C. at a relative humidity (RH) of 75%. The dissolution rates of high purity torsemide Form II Batch Nos. K-26056, K-26057 and K-26058 were identical under both conditions. There was no substantial change in the dissolution rates of any of the present pharmaceutical formulations containing torsemide modification II following 6 weeks of the above storage conditions.

Example 3A. Dissolution of 2.5 mg
High Purity Torsemide modification II Tablets

| | Torsemide dissolved (%) | |
|---|---|---|
| Time (minutes) | K-26056 (2.5 mg) directly after production | K-26056 (2.5 mg) after 6 weeks at 40° C./75% RH |
| 15 | 97 | 98 |
| 30 | 97 | 97 |
| 45 | 97 | 97 |
| 60 | 97 | 97 |

Example 3B. Dissolution of 5 mg High Purity Torsemide modification II Tablets

| Time (minutes) | Torsemide dissolved (%) | |
|---|---|---|
| | K-26057 (5 mg) directly after production | K-26057 (5 mg) after 6 weeks at 40° C./75% RH |
| 15 | 98 | 95 |
| 30 | 98 | 96 |
| 45 | 97 | 95 |
| 60 | 99 | 95 |

Example 3C. Dissolution of 100 mg High Purity Torsemide modification II Tablets

| Time (minutes) | Torsemide dissolved (%) | |
|---|---|---|
| | K-26058 (100 mg) directly after production | K-26058 (100 mg) after 6 weeks at 40° C./75% RH |
| 15 | 87 | 81 |
| 30 | 92 | 84 |
| 45 | 93 | 89 |
| 60 | 93 | 89 |

Example 4

Dissolution Results

The dissolution method used was the U.S.P. Paddle Method, at 50 RPM with purified water at 37° C. For the dissolution test, 6 tablets were tested in 900 mL of purified water according to the Paddle Method of the U.S.P. Example 4B shows the dissolution rates of one representative tablet lot directly after production and after 3 months of storage at 40° C. at a relative humidity (RH) of 75%. The dissolution rates of the high purity toresmide modification II tablet Batch No. K-26683 were identical under both conditions. There was no substantial change in the dissolution rates of any of the present pharmaceutical formulations containing high purity torsemide modification II following 3 months at the above storage conditions.

Example 4A. High purity Torsemide Tablets (100 mg)

| Composition (Batch No. K-26683) | grams per 3,750 tablets |
|---|---|
| High purity Torsemide modification II | 375.0 |
| Lactose Anhydrous NF | 382.5 |
| Crospovidone NF | 180.0 |
| Povidone USP (PVP K-30) | 22.5 |
| Microcrystalline Cellulose NF (Avicel PH 112) | 525 |
| Alcohol USP | 620.00 |
| Magnesium Stearate NF | 15.0 |

EXAMPLE 4B. Dissolution of 100 mg High purity Torsemide modification II Tablets

| Time (minutes) | Torsemide dissolved (%) | |
|---|---|---|
| | K-26683 (100 mg) directly after production | K-26683 (100 mg) after 3 months at 40° C./75% RH |
| 15 | 88 | 88 |
| 30 | 97 | 92 |
| 45 | 98 | 97 |
| 60 | 99 | 98 |

Although certain presently preferred embodiments of the invention have been described herein, it will be apparent to those skilled in the art to which the invention pertains that variations and modifications of the described embodiment may be made without departing from the spirit and scope of the invention. Accordingly, it is intended that the invention be limited only to the extent required by the appended claims and the applicable rules of law.

We claim:

1. A stable pharmaceutical formulation comprising an effective amount of high purity torsemide modification II and a pharmaceutically acceptable carrier, wherein the high purity torsemide modification II does not substantially rearrange into torsemide modification I.

2. The stable pharmaceutical formulation of claim 1, wherein said formulation further comprises lactose anhydrous, crospovidone, povidone, cellulose, and magnesium stearate.

3. The stable pharmaceutical formulation of claim 1, wherein said formulation is a tablet.

4. The stable pharmaceutical formulation of claim 3, wherein the high purity torsemide modification II is present in an amount of about 2.5 to about 200 mg per tablet.

5. The stable pharmaceutical formulation of claim 3, wherein the high purity torsemide modification II is present in an amount of 100 mg per tablet.

6. The stable pharmaceutical formulation of claim 3, wherein the high purity torsemide modification II is present in an amount of about 5 mg per tablet.

7. The stable pharmaceutical formulation of claim 3, wherein the high purity torsemide modification II is present in an amount of 2.5 mg per tablet.

8. The stable pharmaceutical formulation of claim 1, wherein the high purity torsemide modification II does not substantially rearrange into torsemide modification I for at least 3 months.

9. The stable pharmaceutical formulation of claim 1, wherein the high purity torsemide modification II does not substantially rearrange a different polymorphic form of torsemide upon storage at 40°C. and 75% relative humidity for at least 3 months.

10. The stable pharmaceutical formulation of claim 1, wherein the torsemide modification II has a particle size distribution wherein 100% is below 200 μ.

11. The stable pharmaceutical formulation of claim 10, wherein the torsemide modification II has a particle size distribution wherein 100% is below 100 μ.

12. The stable pharmaceutical formulation of claim 11, wherein the torsemide modification II has a particle size distribution wherein 100% is below 50 μ.

13. A stable pharmaceutical formulation comprising a therapeutically effective amount of high purity torsemide modification II wherein the high purity torsemide modification II does not substantially rearrange into torsemide modification I and the dissolution rate in vitro of the formulation, when measured by the U.S.P. Paddle Method at 50–90 RPM in 900 mL water is not less than 80% (by weight) of the high purity torsemide modification II released after 30 minutes.

14. The stable pharmaceutical formulation of claim 13, wherein the dissolution rate in vitro does not substantially change over time.

15. The stable pharmaceutical formulation of claim 14, wherein the dissolution rate in vitro does not substantially change for at least 3 months.

16. A method for treating edema comprising the step of administering to a patient in need of such treatment a therapeutically effective amount of the pharmaceutical formulation of claim 1.

17. A method for treating edema comprising the step of administering to a patient in need of such treatment a therapeutically effective amount of the pharmaceutical formulation of claim 13.

18. The stable pharmaceutical formulation of claim 1, wherein the torsemide modification II has a purity of at least about 99.7% (w/w).

19. The stable pharmaceutical formulation of claim 13, in which the torsemide modification II has a purity of at least about 99.7% (w/w).

* * * * *

UNITED STATES PATENT AND TRADEMARK OFFICE
CERTIFICATE OF CORRECTION

PATENT NO. : 6,482,417 B2
DATED : November 19, 2002
INVENTOR(S) : Leibovici et al.

It is certified that error appears in the above-identified patent and that said Letters Patent is hereby corrected as shown below:

Column 12,
Lines 6 and 9, change "at least" to -- greater than --;
Line 7, change "99.7%" to -- 99.5% --; and
Line 10, change "99.7%" to -- 99.5% --.

Signed and Sealed this

Ninth Day of November, 2004

JON W. DUDAS
*Director of the United States Patent and Trademark Office*